United States Patent
Dickner et al.

(10) Patent No.: US 9,850,014 B2
(45) Date of Patent: Dec. 26, 2017

(54) DEVICE AND METHOD FOR STERILIZING A PACKAGING CONTAINER

(71) Applicant: TETRA LAVAL HOLDINGS & FINANCE S.A., Pully (CH)

(72) Inventors: Jonas Dickner, Påarp (SE); Håkan Mellbin, Hörby (SE); Roger Lindgren, Sövde (SE); Fredrik Hansen, Bjärred (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days.

(21) Appl. No.: 15/115,509

(22) PCT Filed: Jan. 16, 2015

(86) PCT No.: PCT/EP2015/050740
§ 371 (c)(1),
(2) Date: Jul. 29, 2016

(87) PCT Pub. No.: WO2015/113834
PCT Pub. Date: Aug. 6, 2015

(65) Prior Publication Data
US 2017/0166340 A1     Jun. 15, 2017

(30) Foreign Application Priority Data

Jan. 31, 2014 (SE) .................. 1450102

(51) Int. Cl.
*A61L 2/00* (2006.01)
*B01J 19/08* (2006.01)
(Continued)

(52) U.S. Cl.
CPC .............. *B65B 55/08* (2013.01); *A61L 2/087* (2013.01); *A61L 2202/23* (2013.01)

(58) Field of Classification Search
CPC ............ A61L 2/00; B65B 55/00; B65B 31/00
(Continued)

(56) References Cited

U.S. PATENT DOCUMENTS 6,139,796 A    10/2000  Kristiansson et al.
6,140,657 A    10/2000  Wakalopulos et al.
(Continued)

FOREIGN PATENT DOCUMENTS

EP    2 491 955 A1    8/2012
EP    2 746 174 A1    6/2014
(Continued)

OTHER PUBLICATIONS

International Search Report (PCT/ISA/210) dated Mar. 10, 2015, by the European Patent Office as the International Searching Authority for International Application No. PCT/EP2015/050740.
(Continued)

*Primary Examiner* — Monzer R Chorbaji
(74) *Attorney, Agent, or Firm* — Buchanan Ingersoll & Rooney PC

(57) ABSTRACT

The invention relates to a device for sterilization of the interior surface of packaging containers with electron beam, comprising an emitter provided with an electron exit window. The emitter is adapted to emit charge carriers, such as electrons, through the electron exit window, said electrons forming an electron cloud. The device comprises at least one outlet for conditioning at least a sterilized volume in the packaging container. The outlet is adapted to provide a flow of a sterile gaseous medium, thereby generating a first condition at least inside the sterilized volume of the packaging container. The first condition is adapted to prevent any flow of medium from outside the sterilized volume from
(Continued)

Figure 1:
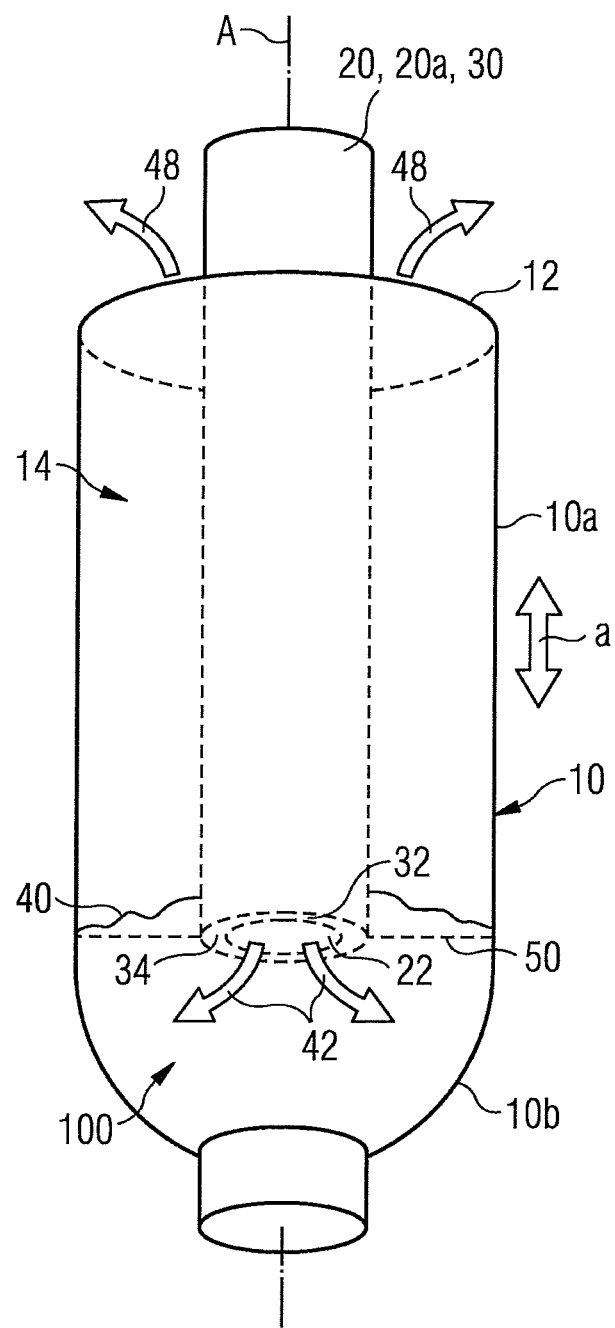

coming into the sterilized volume without first being sterilized by the electron cloud. The invention also relates to a method.

20 Claims, 5 Drawing Sheets

(51) Int. Cl.
   *C07C 1/00* (2006.01)
   *G01N 23/00* (2006.01)
   *B65B 55/08* (2006.01)
   *A61L 2/08* (2006.01)

(58) Field of Classification Search
   USPC ......... 422/32, 186.05, 305–306; 250/455.11;
   204/157.15, 164
   See application file for complete search history.

(56) References Cited

U.S. PATENT DOCUMENTS

| | | | |
|---|---|---|---|
| RE39,657 E | 5/2007 | Wakalopulos et al. | |
| 2008/0073549 A1 | 3/2008 | Avnery | |
| 2008/0138243 A1* | 6/2008 | Kristiansson | A61L 2/087 422/23 |
| 2009/0045350 A1 | 2/2009 | Humele et al. | |
| 2010/0054987 A1 | 3/2010 | Krueger et al. | |
| 2010/0247373 A1 | 9/2010 | Avnery | |
| 2011/0012032 A1 | 1/2011 | Bufano et al. | |
| 2012/0219455 A1 | 8/2012 | Meinzinger et al. | |
| 2012/0294758 A1 | 11/2012 | Avnery | |
| 2013/0015365 A1 | 1/2013 | Bufano et al. | |

FOREIGN PATENT DOCUMENTS

| | | |
|---|---|---|
| WO | WO 97/07024 A1 | 2/1997 |
| WO | WO 00/55884 A1 | 9/2000 |
| WO | WO 2007/095205 A2 | 8/2007 |
| WO | WO 2007/145561 A1 | 12/2007 |
| WO | WO 2014/095838 A1 | 6/2014 |

OTHER PUBLICATIONS

Written Opinion (PCT/ISA/237) dated Mar. 10, 2015, by the European Patent Office as the International Searching Authority for International Application No. PCT/EP2015/050740.

International-Type Search Report (Form ITS/201) dated Sep. 15, 2014 for Application No. 1450102-7.

U.S. Appl. No. 15/115,537, filed Jul. 29, 2016, Dickner et al.

* cited by examiner

DEVICE AND METHOD FOR STERILIZING A PACKAGING CONTAINER

This invention relates to a device and method for sterilizing of the interior surface of a packaging container.

In the prior art different devices and methods for sterilizing packaging materials, in particular packaging container, are known. One method widely used in the prior art is sterilization by means of sterilizing gases and in particular by means of hydrogen peroxide. However, efforts are being made to reduce the use of chemicals when sterilizing containers. Therefore, devices and methods have also become known which sterilize material by means of ultraviolet radiation or electron beams. In general, there is provided an emitter that is adapted to emit charge carriers, in particular electrons, wherein the packaging materials and articles can be sterilized by these charge carriers. For this purpose, the packaging material and the emitter are moved relatively to each other, e. g. an electron gun is put into a bottle-shaped package. However, when the emitter and the packaging material are moved relatively to each other, flows or streams of a medium, such as air, are established in between. If these streams or flows comprise a medium, such as air, that is not sterile, there exists the risk that parts of the packaging material that have already been sterilized are re-infected by the non-sterile flows.

Therefore, it is an object of the current invention to provide a device and method for sterilization of the interior surface of packaging containers that create and/or maintain aseptic conditions inside the packaging container during and after the inside sterilization.

This object is achieved by means of a device according to claim 1 and a method according to claim 16. Additional advantages and features of embodiments of the current invention are defined in the dependent claims.

The device according to the invention comprises an emitter provided with an electron exit window. Said emitter is adapted to emit charge carriers, such as electrons, through the electron exit window. Said electrons form an electron cloud. The device comprises at least one outlet for conditioning at least a sterilized volume in the packaging container. The outlet is adapted to provide a flow of a sterile gaseous medium, thereby generating a first condition at least inside the sterilized volume of the packaging container. The first condition is adapted to prevent any flow of medium from outside the sterilized volume from coming into the sterilized volume without first being sterilized by the electron cloud.

Expediently, the outlet ends in at least one opening such as a nozzle, wherein the nozzle comprises an opening that is preferably round, circular, oval, polygonal or also angled etc. It goes without saying that the outlet is preferably connected with an appropriate piping system, to provide the sterile medium, such as air or for instance nitrogen or other gas or gas mixture. Of course, the device can comprise a plurality of outlets for example two, three, four, five, six and also more. In the following, the term "outlet" is also used in the same way as the term "nozzle", although "nozzle" means strictly speaking only the orifice.

In one or more embodiments the packaging container is basically tube-shaped, and the emitter is adapted for sterilization of at least the interior of the packaging container through an opening of the tube-shaped packaging material. The opening is adapted to enable an insertion of the emitter into the packaging container. The packaging container is closed at its other end portion opposite the opening, and the container extends along an axis. The term "tube-shaped" comprises no limitations concerning the possible form of the cross-section of the packaging container. This means that the cross section can be round, rectangular, circular, polygonal and/or angular and especially, the cross section does not have to be constant along the axis.

The packaging container can for example be made of a plastic material such as for instance PET, or be made of a laminated carton material. With regard to the later a common type of laminated carton material is the ones comprising a core layer of paper or paperboard and one or more barrier layers of, for example, polymer material or aluminium foil. An increasingly common packaging type is the "carton bottle" manufactured in a filling machine in that packaging blanks of the above-described packaging laminate are formed and sealed as a sleeve. Said sleeve is closed in one end in that a top of thermoplastic material is injection moulded directly on the sleeve end portion. The sheets of packaging laminate may be cut from a magazine reel of packaging laminate.

Advantageously, the opening of the packaging container, e.g. the spout or a bottom of the packaging container, has to be big enough so that at least the portion of the emitter comprising the electron exit window can be passed through it, to sterilize in particular the interior surface of the packaging container. In one or more embodiments the emitter has a round, in particular a circular cross section that is basically constant. A diameter of the cross-section lies within a range of about 5-100 mm.

Sterilization is a term referring to any process that eliminates or kills microbial life, including transmissible agents such as for example fungi, bacteria, viruses and spores, which may be present on a surface of the packaging material or in a product. In the (food) packaging industry this is generally referred to as aseptic packaging, i. e. packaging sterilized products in sterilized packaging containers, i. e. keeping both the product and the packaging container free form living germs and microorganisms, so that the freshness of the product can be preserved without special cooling requirements, i. e. so that sterility can be maintained inside a packaging container although it is stored in ambient temperature. In this context the term "commercially sterile" is also commonly used and means in general the absence of microorganisms capable of growing in the food at normal nonrefrigerated conditions at which the food is likely to be held during manufacture, distribution and storage. In this patent application the word "sterile" refers to a condition being at least commercially sterile.

As mentioned above, the first condition is adapted to prevent any flow of medium from outside the sterilized volume from coming into the sterilized volume without first being sterilized by the electron cloud. To stay sterilized, and not risking being re-infected, a sterilized surface and/or volume of air near a sterilized surface cannot have contact with non-aseptic or non-sterile medium/air. In this context it has to be clarified that the medium or the air, respectively, that is provided by the at least one outlet does not have to have a specific mixture. However, it has to be ensured that the medium or the mixture is aseptic or sterile, respectively.

In one or more embodiments the outlet is adapted to be provided within the electron cloud generated by the electrons emitted from the electron exit window. In order for the sterile medium to stay sterile it is necessary to let it flow into a sterile volume. The electron cloud will stay sterile as long as the emitter is in operation and emits electrons.

In one or more embodiments the electron cloud and said flow of sterile gaseous medium together create an aseptic barrier during sterilization. Said aseptic barrier is adapted to prevent any unsterile medium from reaching into the sterilized volume before being sterilized. The electron cloud is the boundary between the sterilized volume of the packaging container and the still unsterilized volume of the same. As long as a flow from outside, i.e. a non-sterile flow, is slow enough, the electron cloud is able to sterilize it before it reaches the sterilized volume of the packaging container. Thus, if controlled, a small un-sterile flow towards the sterilized volume can be accepted.

In one or more embodiments the emitter and the packaging container are adapted to perform a movement relatively to each other between first and second positions. The first position is a position in which the packaging container and the emitter are not engaged with each other. The second position is a position in which an emitter portion, being provided with the electron exit window, is fully inserted into the packaging container, through an opening of the packaging container, for sterilization of the interior surface of the packaging container.

The second position should be deep enough located inside the packaging container so that a sufficient sterilization of the inside of the packaging container especially that side of the container is possible which is located opposite the opening.

The term "relative movement between the emitter and the packaging container" comprises every possible movement arrangement. In one or more embodiments the emitter moves in relation to the packaging container (the packaging container being stationary along the axis). Alternatively, in one or more embodiments the packaging container moves towards and away from the emitter (the emitter being stationary along the axis). The emitter will hence be inserted into the packaging container in that the emitter is received in the packaging container. In other words, the packaging container will be moved to surround the emitter. Alternatively, in one or more embodiments, both the emitter and the packaging container are moved. Each performs a part of the relative movement.

In between the emitter and the packaging container there is formed a gap. The gap can have a constant size or thickness. However, it does not have to be constant. Its size can change when the emitter and the packaging container are moved relatively to each other. This means that the gap can get thicker and/or thinner when the emitter and the packaging container are moved relatively to each other. Inserting the emitter into the packaging container creates basically an outflow of medium out of the packaging container through the opening or through the gap, respectively. The volume of the emitter being inserted forces or pushes air present in the packaging container to flow out of the packaging container, i.e. a flow is created in the gap between the emitter and the packaging container. When instead pulling the emitter out of the packaging container an inflow of medium is created into the packaging container. The inflow compensates for the volume of the emitter leaving the packaging container, i.e. when the emitter leaves the packaging container air is naturally being sucked into the packaging container from outside causing a flow in the gap between the packaging container and the emitter. It goes without saying that the aforementioned inflow would be created in the same way when the emitter does not move and the packaging container is moved away from the emitter. In the same way, an outflow is created when the emitter does not move and the packaging container is moved towards (and pulled over) the emitter. Since the package is light and the emitter is heavy and has a fragile electron exit window many applications is designed such that it is the package that is moving towards and away from the emitter, while the emitter itself is stationary.

In one or more embodiments, during a movement from the second to the first position, the first condition is a flow of sterile gaseous medium being controlled such that a volume of sterile gaseous medium added, per time unit, to the packaging container through the outlet is adapted to at least compensate for the volume of a portion of the emitter leaving the packaging container during the same time unit. In this way any inflow of medium from outside the sterilized volume is not permitted, and the sterilized volume will stay sterile. The flow of sterile medium will make the pressure of the sterilized volume stay the same. It is to be understood that, generally, not the entire emitter is inserted into the packaging container, but a portion of it, namely the portion being provided with the electron exit window. This portion has a volume present in the packaging container. When pulling the emitter out of the packaging container this volume, being present in the packaging container, will decrease. The volume of the sterile medium supplied is to compensate for, or respond to, the "loss of emitter volume" in the packaging container such that the pressure of the sterilized volume can be kept. In other words, the amount of sterile medium per time unit or the flow of the sterile medium, such as air, respectively, that is generated by the at least one outlet is the same or more than the corresponding volume of the emitter that is moved out from the packaging container in the same time unit. Thus, an underpressure can be avoided.

In one or more embodiments, during a movement from the second to the first position, the first condition is a flow of sterile gaseous medium being controlled such that a volume of sterile gaseous medium added, per time unit, to the packaging container through the outlet is adapted to be larger than the volume of a portion of the emitter leaving the packaging container during the same time unit, such that an outflow, or positive flow, of sterile gaseous medium can be created out from the sterilized volume of the packaging container. In this case the first condition is an outflow of the sterile medium out of the sterilized volume, maybe even out of the opening of the packaging container. The outflow works as a barrier and prevents (non-aseptic) medium from outside the sterilized volume from coming into the sterilized volume.

In one or more embodiments, during a movement from the second to the first position, the first condition is a flow of sterile gaseous medium being controlled such that a volume of sterile gaseous medium added, per time unit, to the packaging container through the outlet is adapted to be less than the volume of a portion of the emitter leaving the packaging container during the same time unit, but large enough to prevent any flow of medium from outside the sterilized volume from coming into the sterilized volume without first being sterilized by the electron cloud. The volume of the provided sterile medium does not have to totally compensate for the volume of the emitter portion leaving the packaging container. Part of the volume can be compensated for, and as such, there will be some medium from outside being sucked into the sterilized volume. As long as the non-sterile flow from outside is slow enough, the electron cloud is able to sterilize it before it passes the cloud and reaches further into the sterilized volume of the packaging container. Thus, if controlled, a small un-sterile flow towards the electron cloud can be accepted.

In one or more embodiments the sterilized volume formed inside the packaging container, comprises the electron cloud and is separated from an ambient volume by means of the electron cloud. Hence, the electron cloud is part of the sterilized volume and forms an aseptic barrier towards the environment outside the electron cloud in a direction towards the opening. The walls of the packaging container form the boundary in other directions. The packaging container extends basically along an axis. The electron cloud comprises a width that extends basically perpendicular to the axis, and a length that extends basically along the axis. The width of the electron cloud is large enough to at least cover the packaging container cross section being perpendicular to the axis. This means that the cloud is adapted to cover preferably the entire gap between the emitter and the packaging container. Generally, the gap measures about 1 to 50 mm. Further, the electron cloud or the width of the electron cloud, respectively, is also adapted to cover the diameter of the opening.

In one or more embodiments the device is adapted to control, adjust and/or adapt the flow of the sterile gaseous medium over time. Therefore, expediently an appropriate control unit is provided that is adapted to control the flow of the medium over time. Thus, the flow of the medium does not have to be constant over time but can vary depending on for example a varying gap size or a varying speed of the relative movement.

In one or more embodiment the device comprises a tube, said tube being provided with the outlet. The tube has for example a round, circular, rectangular or polygonal cross section. It may be basically constant, or vary along the length. The tube is hollow.

In one or more embodiments the tube is arranged on the emitter. Either the tube is separate and attached in parallel with the emitter, or the tube is attached on the emitter such that it surrounds the emitter. In both cases the electron exit window is arranged in the vicinity of the outlet, but not shadowed by it. The wording "not shadowed" is meant that the paths of electrons exiting the electron exit window will not be influenced, shaped or stopped by the outlet as such.

In one or more embodiments the emitter extends basically along an axis. The electron exit window is arranged in a plane perpendicular to the axis. The packaging container basically extends along the axis. The relative movement is made along the axis. The tube extends along the emitter.

In one or more embodiments the tube comprises an end surface in the plane of the electron exit window or a plane parallel to the plane of the electron exit window. Said end surface comprises the at least one outlet. In one or more embodiments, where the tube surrounds the emitter, the outlet is for example basically ring-shaped, and is provided at the periphery of the electron exit window. In one or more embodiments, where the tube is attached and parallel to the emitter, the outlet is for example circular.

In one or more embodiments the tube comprises an outer envelope surface in the vicinity of the electron exit window. The outer envelope surface comprises the at least one outlet. The outer envelope surface is the cylindrical outer surface of the emitter. As mentioned before, the tube can be arranged to surround the emitter, and as such the outer envelope surface of the tube can be arranged with one or more outlets. The shape of the outlet can be of any design, for example circular, oval, rectangular or polygonal. The flow of the medium that comes out of the at least one outlet can be directed basically tangentially and/or radially to the axis.

In one or more embodiments the device is arranged in an irradiation chamber in a filling machine, which filling machine also comprises at least one filling station for filling content into the packaging container, and at least one station for sealing the opening after filling. For example, a plurality of emitters can be provided on a carousel or the like which is adapted to rotate (see for instance the international publication No. WO2014/095838 filed by the applicant). The packaging containers, which are transported for example via a conveyor, reach the carousel and are aligned with one of the (rotating) emitters. During at least a part of one rotation of the carousel, the interior sterilization takes place. The packaging container is lifted to surround the emitter and then lowered again, i.e. the relative movement takes place. The lifting is performed by lifters provided in the conveyor. After the inside sterilisation the packaging container leaves the carousel by means of the conveyor. Therefore, dependent on the size of the carousel, the number of the emitters arranged at the carousel and/or the rotation speed of the carousel, a certain span of time for sterilization is available.

In one or more embodiments the emitter is non-sterile and the sterilization of the interior surface of the packaging container is performed during a relative movement between the emitter and packaging container, from the second to the first position, at so called run-out. In general, during a run-in (movement from first to second position) or during inserting the emitter, respectively, into the packaging material or vice versa, it is difficult to avoid risk for re-infection, because of the unsterile emitter. Therefore, only the run-out is used for sterilization. Run-in is considered wasted from a sterilization point of view. Therefore, one possibility is to make the time-span for run-out as long as possible or at least longer than the time span for run-in. Doing this, the inflow can more easily be controlled so that it can be sterilized by the cloud of electrons during pull-out of the emitter.

The invention also relates to a method for sterilizing the interior surface of packaging containers with electron beam. The method comprises the step of providing an emitter provided with an electron exit window, said emitter being adapted to emit charge carriers, such as electrons, through the electron exit window, said electrons forming an electron cloud. The method further comprises the step of conditioning at least a sterilized volume inside a packaging container. Such step comprises the sub-steps of providing a flow of a sterile gaseous medium, and generating, by said flow, a first condition at least inside the sterilized volume of the packaging container. The first condition is adapted to prevent any flow of medium from outside the sterilized volume from coming into the sterilized volume without first being sterilized by the electron cloud.

In one or more embodiments the method comprises the step of providing the flow of the sterile gaseous medium through an outlet, said outlet being adapted to be arranged within the electron cloud.

In one or more embodiments the method comprises the step of moving the emitter and the packaging container relatively to each other between first and second positions. The first position is a position in which the packaging container and the emitter are not engaged with each other. The second position is a position in which an emitter portion, being provided with the electron exit window, is fully inserted into the packaging container, through an opening of the packaging container, for sterilization of the interior surface of the packaging container.

In one or more embodiments the method comprises the step of moving from the second to the first position, and during that movement, generating the first condition by controlling the flow of sterile gaseous medium such that a volume of sterile gaseous medium being added, per time unit, to the packaging container through the outlet is adapted to at least compensate for the volume of a portion of the emitter leaving the packaging container during the same time.

In one or more embodiments the method comprises the steps of moving from the second to the first position, and during that movement, generating the first condition by controlling the flow of sterile gaseous medium such that a volume of sterile gaseous medium being added, per time unit, to the packaging container through the outlet is adapted to be larger than the volume of a portion of the emitter leaving the packaging container during the same time, such that a flow of sterile gaseous medium can be created out from the sterilised volume of the packaging container.

In one or more embodiments comprises the steps of moving from the second to the first position, and during that movement, generating the first condition by controlling the flow of sterile gaseous medium such that a volume of sterile gaseous medium being added, per time unit, to the packaging container through the outlet is adapted to be less than the volume of a portion of the emitter leaving the packaging container during the same time, but large enough to prevent any flow of medium from outside the sterilized volume from coming into the sterilized volume without first being sterilized by the electron cloud.

Additional advantages and features of the current invention are shown in the following description of embodiments of the current invention with reference to the attached drawings. Single features or characteristics of respective embodiments are explicitly allowed to be combined with the scope of the current invention.

Figure 2:
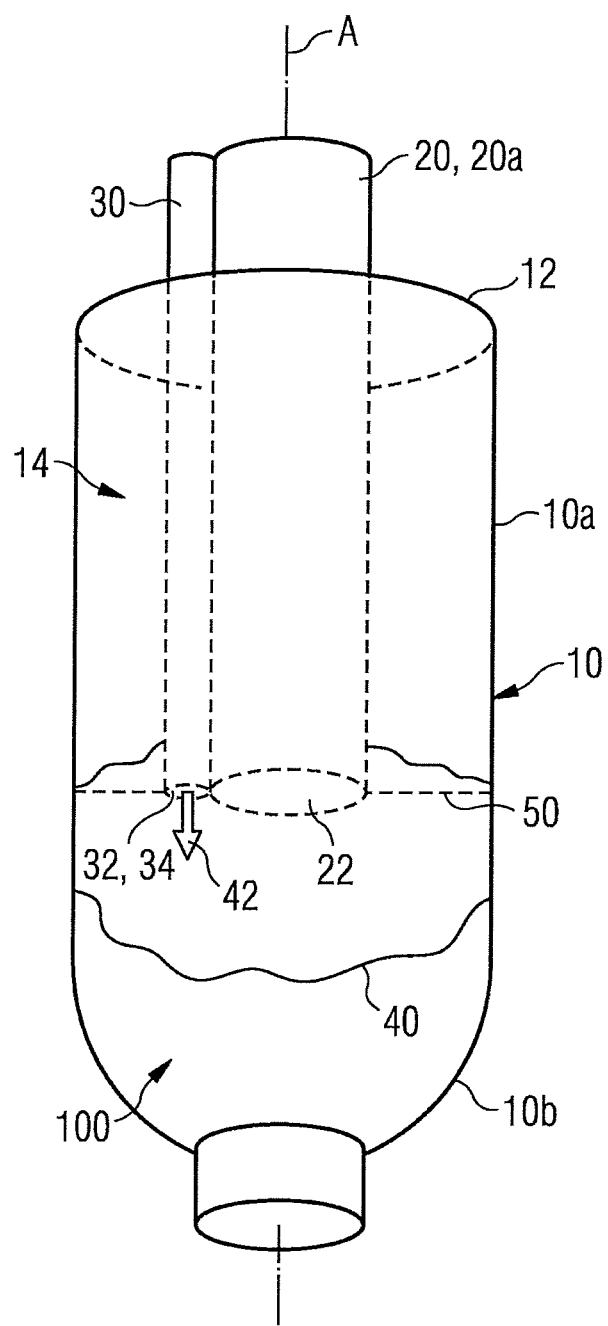
Figure 3:
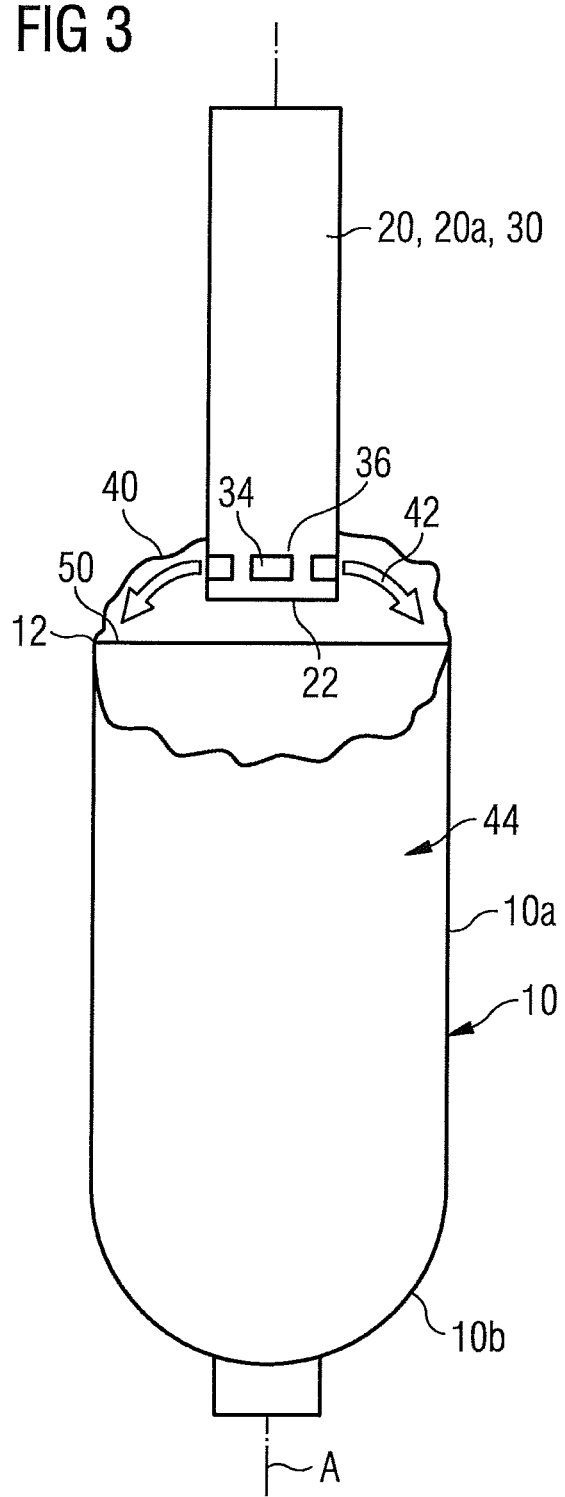
Figure 4:
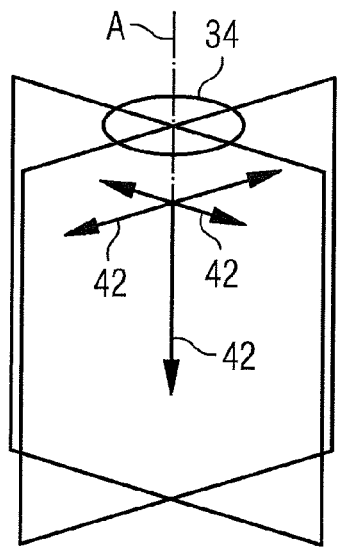
Figure 5:
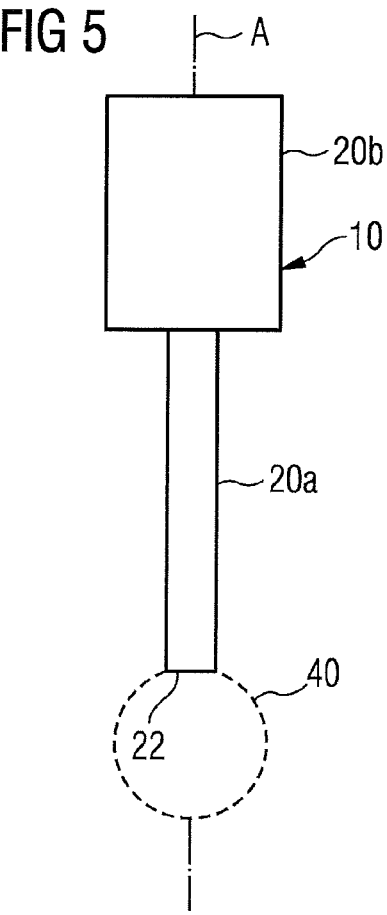
Figure 6:
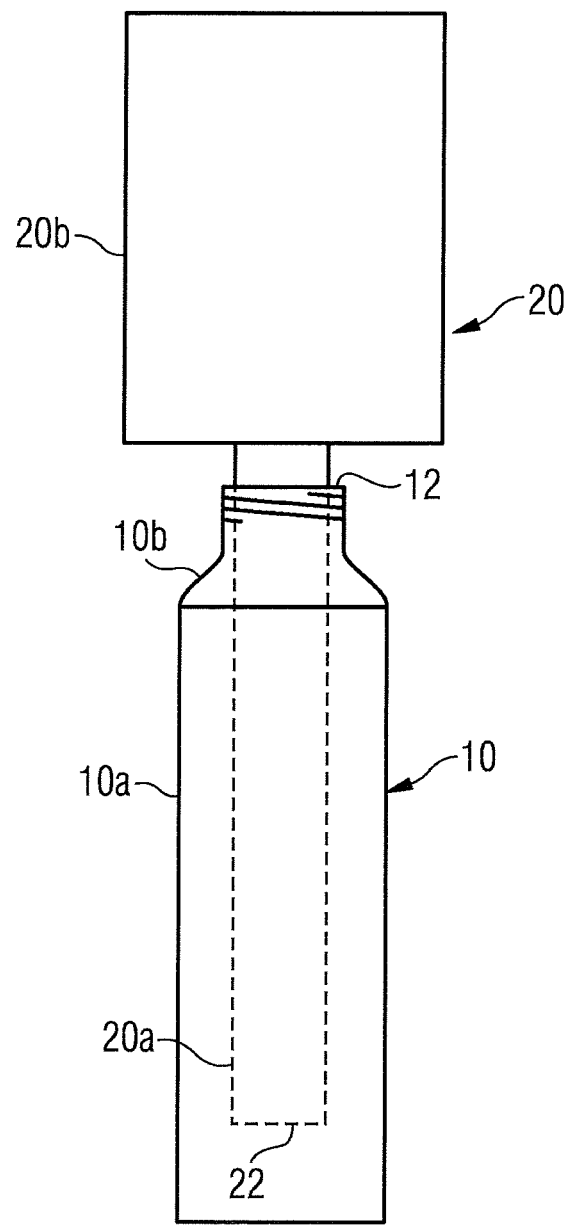

FIG. 1: shows schematically a first embodiment of the invention and a packaging container in a second position;

FIG. 2: shows schematically a second embodiment of the invention and a packaging container in a position between the first and second positions;

FIG. 3: shows schematically a third embodiment of the invention and a packaging container in a first position;

FIG. 4: shows a basic scheme of an outlet that is adapted to guide a flow of a medium along different directions;

FIG. 5: shows an emitter;

FIG. 6: shows an emitter and a packaging container.

Referring now to FIG. 1 a packaging container 10 is shown that extends basically along an axis A. The packaging container 10 is basically tube-shaped and comprises an opening 12. In particular, the packaging container is in a shape ready to be filled with product through the opening 12. It comprises a sleeve body 10*a* and a top portion 10*b*. The top portion 10*b* comprises a neck or spout sealed with for example a screw cap or other closure. The sleeve body 10*a* is provided with the opening 12. In this embodiment the opening 12 of the packaging container 10 is an open bottom end, facing upwards in the figure, which after filling will be sealed and folded to form a substantially flat bottom surface.

Inside the packaging container 10 a tube 30 and an emitter 20 are arranged or located. The emitter 20 is provided with an electron exit window 22, arranged in a plane perpendicular to the axis A, and will be more described with regard to FIG. 5. However, it is to be mentioned that only a portion of the emitter 20 is shown in FIG. 1 namely a first cylindrical body 20*a* (see FIG. 5). The tube 30 surrounds the emitter 20, and thus the emitter 20 is not strictly speaking visible in FIG. 1, but hidden inside the tube. The tube 30 may be an outer shell of the first cylindrical body 20*a* of the emitter 20. The emitter 20 comprises an end surface 32 in the plane of the electron exit window 22, or alternatively a plane parallel to the plane of the electron exit window 22. They may be arranged on different levels. The end surface 32 comprises an outlet 34. In this embodiment the outlet is basically ring-shaped. It is arranged around the periphery of the electron exit window 22.

The emitter is adapted to emit electrons which exits the emitter through the electron exit window 22 and forms an electron cloud 40 outside said window. The outlet 34 is arranged such that it will be in the electron cloud 40 during operation of the emitter.

The outlet 34 is adapted to provide a flow 42 of a medium. The medium may be sterile air or another gas such as for example nitrogen, or a mixture of gases. The gas is fed from a (not visible) supply and through an inner channel in the tube 30. The inner channel may be formed by the entire space, or a part of the space, between an inner tube surface and an outer envelope surface of the cylindrical body 20*a*. Alternatively, there may be arranged conduits in the tube. Since the outlet 34 is arranged such that it will be in the electron cloud 40, the flow of the sterile air will naturally be directed into the electron cloud 40.

The emitter 20 and the packaging container 10 are adapted to perform a movement relatively to each other between first and second positions such that sterilization of the inside surface of the packaging container can be made. The relative movement is illustrated as arrow a in FIG. 1. The movement is made along axis A. The inside surface of the packaging container 10 is sterilized by the electron cloud 40 emitted from the emitter 20. The first position is a position in which the packaging container 10 and the emitter 20 are not engaged with each other, see FIG. 3, whereas the second position is shown in FIG. 1. In the second position an emitter portion, being at least a portion of the first cylindrical body 20*a* provided with the electron exit window 22, is fully inserted into the packaging container 10 through the opening 12. The electron cloud 40 then fills up the entire top portion 10*b* of the packaging container, i.e. the volume farthest away from opening 12. During a sterilization cycle, i.e. during sterilization of a packaging container, movement is performed from the first position to the second position, and from the second position back to the first position.

A movement from the first to the second position, i.e. a relative movement of the emitter and the packaging container towards each other along axis A, will naturally cause an outflow of gaseous medium in a gap 14 between the emitter and the packaging container 10. Gaseous medium in the packaging container will flow out of the packaging container. A movement from the second position to the first position, i.e. a relative movement of the emitter and the packaging container away from each other along axis A, will naturally cause an inflow of gaseous medium in the gap between the emitter and the packaging container. Gaseous medium from outside will flow into the packaging container.

In an application where the emitter is non-sterile, and the irradiation chamber in which the emitter is arranged is not sterilized, an outflow of medium from the packaging container is of less concern from an aseptic point of view than an inflow. When packaging container interior sterilization has begun any uncontrolled inflow of un-sterile medium should be avoided not to re-infect a sterilized volume 44 inside in the packaging container.

In this and the following embodiments the actual sterilization of the inside surface of the packaging container is made during a movement between the second position and the first position, and hence, as mentioned above, the object of this invention is to condition the sterilized volume 44 in the packaging container 10 in order to control any potential inflow to avoid re-infection.

It should of course be understood that the emitter may be in continuous operation, and as such it is of course also irradiating the packaging container during movement from the first to the second position. However, due to the risk of re-infection, only the dose given when moving from the second position to the first position is considered to be the one sterilizing.

In the following the sterilization cycle will be described. The sterilization cycle starts with a movement from the first to the second position (the second position being shown in FIG. 1). In the embodiment shown in FIG. 1 the emitter is stationary along axis A and the packaging container is the lifted, upwards in the figure, to surround the emitter. The lifting may be accomplished by a packaging container lifter and may be made quick. There is no need to consider or take any measures with regard to any flows of un-sterile medium out of the packaging container from inside the packaging container.

In FIG. 1 the sterilized volume 44 is the volume of the electron cloud 40 filling the top portion of the packaging container 10.

In a next step the packaging container will start to be slowly lowered from its position around the emitter 20. The sterilized volume 44 will increase as the lowering continues (see for example FIG. 2). At the same time a flow 42 of a sterile gaseous medium is provided from the outlet 34 to generate a first condition at least inside the sterilized volume 44 of the packaging container 10. A description of the first condition will follow.

In a final step of the sterilization cycle the packaging container 10 has been lowered so much that the emitter 20 is no longer inside the packaging container 10 (see for example FIG. 3). The first position has been reached again. The electron cloud 40 still protects the opening 12 of the packaging container 10, and the packaging container can for example be moved into an overlapping electron cloud of other emitters provided for sterilization of the outer surface of the packaging container.

As mentioned above, the object of this invention is to condition the sterilized volume 44 in the packaging container 10 in order to control any potential inflow to avoid re-infection. In the following the conditioning of the sterilized volume will be described.

The first condition is adapted to generally prevent any flow of medium from outside the sterilized volume 44 from coming into the sterilized volume 44 without first being sterilized by the electron cloud 40. This can be accomplished in that a volume of sterile gaseous medium is added, per time unit, to at least compensate for the volume of a portion of the emitter 20 leaving the packaging container 10 during the same time. When the emitter is leaving the packaging container, i.e. when the packaging container is lowered from the emitter, there can be created an inflow of medium from outside to fill the volume left by the emitter. Such inflow can be prevented by instead letting the sterile gaseous medium fill the volume. A control unit adapts the flow of the sterile medium in relation to the speed of the relative movement and the size of the gap 14 between the emitter 20 and the packaging container 10.

Alternatively, a volume of sterile gaseous medium is added, per time unit, which is larger than the volume of a portion of the emitter 20 leaving the packaging container 10 during the same time, In such case there is created an outflow 48 of sterile gaseous medium out from the sterilized volume 44 of the packaging container 10. This outflow 48 is illustrated by the arrows in FIG. 1.

Another alternative is to add a volume of sterile gaseous medium, per time unit, which is less than the volume of a portion of the emitter 20 leaving the packaging container 10 during the same time. However, this volume of sterile gaseous medium needs to be large enough to prevent any flow of medium from outside coming into the sterilized volume 44 without first being sterilized by the electron cloud 40. This means that the flow of medium from outside coming into the cloud 40 needs to have a speed slow enough such that the cloud 40 manage to sterilize it before it leaves the cloud 40. In other words, an un-sterile medium needs to stay within the cloud 90 for a certain time in order to be sterilized. How long this time is depends for example on the dose rate of the emitter 20 and the flow speed.

The electron cloud 40 and the flow 42 of sterile gaseous medium together create an aseptic barrier 50 during sterilization. The aseptic barrier is shown in for example FIG. 1 as a dashed line through the electron cloud 40. The barrier 50 is created at a level, along axis A and closest to the opening 12, where the electron cloud contacts the interior surface of the packaging container along a continuous perimeter line. In the second position the aseptic barrier 50 can be created by the electron cloud 40 only, but during the movement from the second to the first position the aseptic barrier is created by the electron cloud together with the flow of sterile medium. Said aseptic barrier 50 is adapted to prevent any unsterile medium from reaching into the sterilized volume 44 before being sterilized.

FIG. 2 shows a second embodiment of the invention. Only the differences from the first embodiment will be described. In the second embodiment the emitter 20 and the tube 30 is arranged side by side, and the tube 30 extends along the emitter 20, and along the axis A. The tube 30 is attached to the outer envelope surface of the emitter 20. As with the first embodiment, the tube 30 in this embodiment comprises an end surface 32 in the plane of the electron exit window 22 or in a plane parallel to the plane of the electron exit window 22. The end surface 32 comprises the at least one outlet 34.

In FIG. 2 the aseptic barrier 50 is shown as a dashed lined arranged slightly above the electron exit window 22 and the outlet 34.

FIG. 3 shows a third embodiment of the invention being a variation of the first embodiment. As with the first embodiment the tube 30 of the third embodiment is surrounding the emitter 20 (making the emitter non-visible in the figure). Instead of having an output directed downwards, like the first embodiment, there are several outlets provided in an outer envelope surface 36. The outlets are arranged in the vicinity of the electron exit window 22 such that they, during operation of the emitter, will be located in the electron cloud 40.

In FIG. 3 the aseptic barrier 50 is at the same level as the opening 12 of the packaging container 10.

FIG. 4 shows a basic scheme of an outlet 34 wherein different flow directions of a flow 42 are visualized by the different arrows. The arrows reveal that different flow directions can be established out of the outlet 34. It goes without saying that the flow 42 does not have to be directed strictly along the arrows. All intermediate directions are also possible.

FIG. 5 shows an exemplary emitter 20 for sterilizing the interior of ready-to-fill packaging containers 10.

The emitter 20 comprises an electron generator for emitting a substantially circular electron beam along a path. The electron generator is enclosed in a hermetically sealed vacuum chamber, in a second cylindrical body 20b of said vacuum chamber.

The electron generator comprises a cathode housing and a filament (not visible). In use, an electron beam is generated by heating the filament. When an electrical current is fed through the filament, the electrical resistance of the filament causes the filament to be heated to a temperature in the order of 2000° C. This heating causes the filament to emit a cloud of electrons. The electrons are accelerated towards an electron exit window 22 by means of a high-voltage potential between the cathode housing and the exit window (being the anode). Subsequently, the electrons pass through the electron exit window 22 and continue towards the target area, i.e. in this case the inside of the packaging container 10.

The filament can be made of tungsten. A grid may be placed between the filament and an electron beam exit window. It is provided with a number of openings and is used for diffusing the electron beam into a more uniform beam, and for focusing the electron beam towards the target area.

The high-voltage potential is created by for example connecting the cathode housing and the filament to a power supply and by connecting the vacuum chamber to ground. The filament also needs a second connection. The emitter 20 is generally denoted low voltage electron beam emitter if the voltage is below 300 kV. In the disclosed design the accelerating voltage is in the order of 95 kV. This voltage results in a kinetic (motive) energy of 95 keV in respect of each electron. However, another voltage can be chosen, for example in the interval 75-150 kV. By applying an electrical potential also to the previously mentioned control grid the emission of electrons may be further controlled. If a separate and variable electrical potential is applied to the control grid it makes it possible to use the control grid for active shaping of the generated electron beam. For these purposes the control grid may be electrically connected to a separate power supply.

The emitter 20 is, as mentioned, further provided with an electron exit window 22. The window 22 can be made of a metallic foil, such as for example titanium, and can have a thickness in the order of 4-12 µm. A supporting net (not shown) formed of aluminum or copper supports the foil from inside the vacuum chamber. The electrons are exiting the vacuum chamber through the exit window 20.

The vacuum chamber is made up of two elongate cylindrical bodies 20a, 20b with substantially circular cross sections. The cylindrical bodies have a common longitudinal centre axis. The first cylindrical body 20a has an end surface, in a plane being perpendicular to the centre axis, being provided with the electron exit window 22. The electron exit window 22 is circular and preferably extends over most of the end surface. The diameter of said first body 20a is small enough to be inserted into the ready-to-fill packaging container 10, the cross section of said first body is dimensioned such that it can be guided through the opening 12 of the packaging container 10. The second body 20b is provided with the electron beam generator, and the diameter of said second body 20b is larger than the first body 20a. The diameter of the emitted electron beam, while still inside the emitter 20, is smaller than the diameter of the first body 20a.

The emitter 20 emits, from its electron exit window 22, an electron cloud 40 illustrated schematically by a line in FIG. 5. The cross sectional shape is somewhat circular, as shown, or droplet-shaped. The shape of the electron cloud is defined by the shape of the electron exit window 22 and by the Brownian motion of individual electrons leaving the electron exit window. The electron cloud is axis-symmetrical, around axis a, and the cloud volume is thereby spherical (or droplet-shaped). In the centre of the electron cloud 40 the dose rate is higher. The energy of the emitter 20 needs to be matched with the sterilization time available, the packaging container size and shape, the packaging container velocity relative the electron beam emitter, and the above number should be seen purely as an example.

In the embodiments described above the opening 12 of the packaging container 10 is an open bottom end, which after filling will be sealed and folded to form a substantially flat bottom surface. It should however be understood that this opening 12, through which the emitter 20 is received and through which filling will be made, may instead be arranged in the top portion 10b of the packaging container, as a neck or spout portion of the packaging container 10. FIG. 6 illustrates such. The neck or spout portion will, after filling, be sealed by for instance a screw cap.

The device according to the invention can be arranged in an irradiation chamber in a filling machine. The filling machine comprises at least one filling station for filling content into the packaging container and at least one station for sealing the opening after filling. The invention can for example be applied in the sterilization device as described in the international publication No. WO2014/095838 filed by the applicant. During interior sterilization of the packaging containers a relative movement is made between the packaging container and the emitter. A plurality of emitters are provided on a carousel or the like which is adapted to rotate. The packaging containers, which are transported for example via a conveyor, reach the carousel and are attached to one of the (rotating) emitters. During at least a part of one rotation of the carousel, the sterilization takes place and the packaging container is removed from the appropriate emitter or from the carousel, respectively.

REFERENCE NUMERALS 10 packaging container
10a sleeve body
10b top portion
12 opening
14 gap
20 emitter
20a first cylindrical body
20b second cylindrical body
22 electron exit window
30 tube
32 end surface
34 outlet
36 outer envelope surface
40 electron cloud
42 flow (of the medium)
44 sterilized volume
48 outflow
50 aseptic barrier
A axis
a arrow

The invention claimed is:

1. Device for sterilization of an interior surface of a packaging container with electron beam, comprising:
   an emitter provided with an electron exit window, said emitter being adapted to emit charge carriers through the electron exit window, said electrons forming an electron cloud;
   at least one outlet for conditioning at least a sterilized volume in an interior of the packaging container, the packaging container comprising a first end and a second end opposite to the first end in an axial direction of the packaging container;

wherein the outlet is adapted to provide a flow of a sterile gaseous medium, thereby generating a first condition at least inside the sterilized volume of the packaging container, the outlet being positioned within the interior of the packaging container at an intermediate position in the axial direction between the first and second ends of the packaging container when the outlet provides the flow of the sterile gaseous medium; and wherein the first condition is adapted to prevent any flow of medium from outside the sterilized volume from coming into the sterilized volume without first being sterilized by the electron cloud.

2. Device according to claim 1, wherein the outlet is adapted to be provided within the electron cloud generated by the electrons emitted from the electron exit window.

3. Device according to claim 2, wherein said electron cloud and said flow of sterile gaseous medium together create an aseptic barrier during sterilization, and wherein said aseptic barrier is adapted to prevent any unsterile medium from reaching into the sterilized volume before being sterilized.

4. Device according to claim 1, wherein the emitter and the packaging container are adapted to perform a movement relatively to each other between first and second positions, wherein the first position is a position in which the packaging container and the emitter are not engaged with each other, and wherein the second position is a position in which an emitter portion, being provided with the electron exit window, is fully inserted into the packaging container, through an opening of the packaging container, for sterilization of the interior surface of the packaging container.

5. Device according to claim 4, wherein, during a movement from the second to the first position, the first condition is a flow of sterile gaseous medium configured to be controlled such that a volume of sterile gaseous medium added, per time unit, to the packaging container through the outlet is adapted to at least compensate for the volume of a portion of the emitter leaving the packaging container during the same time unit.

6. Device according to claim 4, wherein, during a movement from the second to the first position, the first condition is a flow of sterile gaseous medium configured to be controlled such that a volume of sterile gaseous medium added, per time unit, to the packaging container through the outlet is adapted to be larger than the volume of a portion of the emitter leaving the packaging container during the same time unit, such that an outflow of sterile gaseous medium can be created out from the sterilized volume of the packaging container.

7. Device according to claim 4, wherein, during a movement from the second to the first position, the first condition is a flow of sterile gaseous medium configured to be controlled such that a volume of sterile gaseous medium added, per time unit, to the packaging container through the outlet is adapted to be less than the volume of a portion of the emitter leaving the packaging container during the same time unit, but large enough to prevent any flow of medium from outside the sterilized volume from coming into the sterilized volume without first being sterilized by the electron cloud.

8. Device according to claim 1, wherein the sterilized volume is formed inside the packaging container, comprises the electron cloud and is separated from an ambient volume by means of the electron cloud.

9. Device according to claim 1, wherein the device is adapted to control, adjust and/or adapt the flow of the sterile gaseous medium over time.

10. Device according to claim 1, wherein the device comprises a tube, said tube being provided with the outlet.

11. Device according to claim 10, wherein the tube is arranged on the emitter.

12. Device according to claim 10, wherein the emitter extends basically along an axis, wherein the electron exit window is arranged in a plane perpendicular to the axis, wherein the emitter is adapted to be axially inserted along an extension of the packaging container, wherein the relative movement is made along the axis, and wherein the tube extends along the emitter.

13. Device according to claim 12, wherein the tube comprises an end surface in the plane of the electron exit window or a plane parallel to the plane of the electron exit window, and wherein the end surface comprises the at least one outlet.

14. Device according to claim 12, wherein the tube comprises an outer envelope surface in the vicinity of the electron exit window, wherein the outer envelope surface comprises the at least one outlet.

15. Device according to claim 1, wherein the device is arranged in an irradiation chamber in a filling machine, which filling machine also comprises at least one filling station for filling content into the packaging container, and at least one station for sealing the opening after filling.

16. Method for sterilizing an interior surface of a packaging container with electron beam, the method comprising:

positioning an emitter inside the packaging container, the emitter including an electron exit window emitting charge carriers through the electron exit window to form an electron cloud, conditioning at least a sterilized volume inside the packaging container comprising introducing a flow of a sterile gaseous medium inside the container from an outlet positioned inside the packaging container when the flow of the sterile gaseous medium is introduced, the outlet being movable relative to the packaging container while the outlet is positioned inside of the packaging container and the flow of the sterile gaseous medium is being introduced, and generating, by said flow, a first condition at least inside the sterilized volume of the packaging container that prevents any flow of medium outside the sterilized volume from coming into the sterilized volume without first being sterilized by the electron cloud.

17. Device for sterilizing an interior surface of a packaging container with electron beam comprising:

an emitter comprised of a body that houses a sealed vacuum chamber in which is produced electrons, the body including a free end portion configured to be positioned inside the packaging container and at which is located an electron exit window from which is emitted the electrons while the electron exit window at the free end portion of the body is located in the packaging container to form an electron cloud in the packaging container that produces a sterilized volume in the packaging container;

the emitter and the packaging container being relatively movable so that the emitter moves between one position in which the electron exit window at the free end portion of the body is positioned inside the packaging container to an other position in which the electron exit window at the free end portion of the body is positioned outside the packaging container; and a sterile gaseous medium tube configured to be connected to a sterile gaseous medium source, the tube being connected to the emitter so that relative movement between the emitter and the packaging container results in relative movement between the sterile gaseous medium tube and the packaging container, the sterile gaseous medium tube including an outlet from which the sterile gaseous medium tube flows and enters the packaging container to prevent any flow of medium outside the sterilized volume from coming into the sterilized volume without first being sterilized by the electron cloud.

18. The device according to claim 17, wherein the sterile gaseous medium tube is attached to a side of the emitter.

19. The device according to claim 17, wherein the sterile gaseous medium tube is coaxial with the emitter.

20. The device according to claim 17, wherein both the tube and the emitter are positioned within the interior of the package when the emitter is at the one position in which the electron exit window is positioned inside the packaging container.

* * * * *